United States Patent [19]
Bräther et al.

[11] 3,971,949
[45] July 27, 1976

[54] OPERATIVE LOCATION FOR THE EXAMINATION OF PATIENTS BY MEANS OF X-RAYS

[75] Inventors: Wolfgang Bräther; Alfred Hahn, both of Erlangen, Germany

[73] Assignee: Siemens Aktiengesellschaft, Erlangen, Germany

[22] Filed: Oct. 9, 1974

[21] Appl. No.: 513,493

[30] Foreign Application Priority Data
Oct. 13, 1973  Germany............................ 2351542

[52] U.S. Cl.............................. 250/446; 250/445 R; 250/468; 250/491
[51] Int. Cl.²......................................... G01M 23/00
[58] Field of Search ........... 250/444, 445, 453, 468, 250/470, 490, 491, 523, 446

[56] References Cited
UNITED STATES PATENTS

| | | | |
|---|---|---|---|
| 2,795,702 | 6/1957 | Morris | 250/470 |
| 3,281,598 | 10/1966 | Hollstein | 250/445 |
| 3,448,979 | 6/1969 | Farmer | 250/470 |
| 3,671,742 | 6/1972 | Browning | 250/470 |
| 3,792,264 | 2/1974 | Lacey | 250/470 |
| 3,855,476 | 12/1974 | Farmer | 250/470 |

*Primary Examiner*—Alfred E. Smith
*Assistant Examiner*—B. C. Anderson
*Attorney, Agent, or Firm*—Haseltine, Lake & Waters

[57] ABSTRACT

An operative location or station for the examination of patients by means of X-rays, including a patients' support bed which is tiltable about a horizontal, vertically adjustable pivoting axis; including an X-ray exposure or filming installation having a picture plane oriented in parallel with the patients' support bed; a so-called overhead X-ray tube which is directed towards the picture plane; and an automatic developing arrangement for the sheets of film. The operative location is provided with transport means for the exposed film sheets which are compensatory for the vertical adjustability and inclinability of the X-ray exposure installation between the picture plane and the automatic developing arrangement, the latter of which is immovably located on the floor.

10 Claims, 4 Drawing Figures

OPERATIVE LOCATION FOR THE EXAMINATION OF PATIENTS BY MEANS OF X-RAYS

FIELD OF THE INVENTION

The present invention relates to an operative location or station for the examination of patients by means of X-rays, including a patients' support bed which is tiltable about a horizontal, vertically adjustable pivoting axis; including an X-ray exposure or filming installation having a picture plane oriented in parallel with the patients' support bed; a so-called overhead X-ray tube which is directed towards the picture plane; and an automatic developing arrangement for the sheets of film.

DISCUSSION OF THE PRIOR ART

Known is an X-ray examining apparatus having a patients' support bed or pallet which is tiltable about a horizontal, vertically adjustable pivoting axis, including an X-ray exposure installation having a picture plane oriented in parallel with the patient support bed; and an overhead X-ray tube directed towards the picture plane. In this prior art X-ray examining apparatus, whose X-ray exposure installation is supplied with film material from a supply magazine, the exposed film sheets are stored in a collecting magazine which is mounted on the film exposure installation. This collecting magazine must be removed from time to time from the X-ray examining apparatus by a special servicing personnel, and conveyed into a darkroom in which the exposed film sheets are removed from the collecting magazine and then transmitted to an automatic developing arrangement. In this instance, it has been found to be disadvantageous that the X-ray examining apparatus is blocked off during the removal of the collecting magazine, the emptying of the latter in the darkroom, and the remounting thereof on the X-ray exposure installation. A further disadvantage of the prior art apparatus lies in the need for the additionally required servicing personnel.

SUMMARY OF THE INVENTION

Accordingly, it is an object of the present invention to provide a more uninterrupted operative sequence for such known X-ray examining apparatus and, in particular, to avoid the need for employment of a special servicing personnel. In an operative location of the above-mentioned type there are provided transport means for the exposed film sheets which are compensatory for the vertical adjustability and inclinability of the X-ray exposure installation between the picture plane and the automatic developing arrangement, the latter of which is immovably located on the floor. This then will create the condition for the self-actuated conveyance of the exposed film sheets from out of the exposure installation to the automatic developing arrangement for all operatively adjustable elevations and inclined positions of the X-ray exposure installation.

In a particularly advantageous embodiment of the invention, a conveying run for the exposed film sheets may be attached to the X-ray exposure installation, and be pivotally supported about the pivoting axis together with the latter, and in which there also may be utilized at least one vertically adjustable intermediate magazine centerable interchangeably with respect to the conveying run and to the automatic developing arrangement, which is pivotable about a support axis extending in parallell with the pivoting axis. This embodiment permits that film sheets to be transferred out of the exposure installation at any inclined position of the X-ray exposure installation along the conveying run into the intermediate magazine which is centered or aligned relative to the conveying run. By means of this intermediate magazine, the exposed film sheets may in accordance with a particular need, as for example, a change of patients, through movement of the intermediate magazine, be transferred into the attached automatic exposure arrangement.

The centering or alignment of the intermediate magazine with the conveying run may be carried out in a particularly simple and dependable manner in the various inclined positions of the conveying run when, in a suitable further modification of the invention, a guide bracket for the exposed film sheets is mounted on the conveying run, and wherein a guide element associated with the guide bracket is fastened onto the intermediate element, by means of which the intermediate magazine, upon approaching to the conveying run, is rotatable and centerable or alignable in the respective inclined position of the conveying run. Upon lowering of the intermediate magazine, the guide element which is located at the bottom side of the intermediate magazine engages with the guide bracket which is fastened to the conveying run, and rotates the intermediate magazine into the respective identical inclined position as is the conveying run.

In order to enhance the state of filming preparedness of the X-ray examining apparatus, in an advantageous further embodiment of the invention, there may be provided coupling means for taking along of the intermediate magazine during a change in the position of the X-ray exposure installation, and which connects the conveying run with the intermediate magazine. Consequently, it becomes possible that even during tilting movement of the X-ray exposure installation, in effect, to immediately thereafter complete X-ray exposures. Thus, there is no longer any need to await the intermediate magazine to be centered or aligned in its new position.

The unloading of the intermediate magazine into the automatic developing arrangement may be significantly accelerated when, in an advantageous embodiment of the invention, the automatic developing arrangement has positioned immediately preceding it, a collecting magazine for the undeveloped film sheets. Thereby, during unloading of the intermediate magazine, no further consideration need be given to the processing speed of the automatic developing arrangement. The film sheets which are stored in the intermediate magazine may be transferred within a few seconds into the collecting magazine, so that the intermediate magazine may again be connected to the conveying run within the shortest time. The exposed film sheets which have been transferred into the collecting magazine, independently of the position of the intermediate magazine, are withdrawn from the collecting magazine by the automatic developing arrangement in conformance with the latters processing speed.

A particularly simple construction of the operative location or station may be attained when, in another embodiment of the invention, there is positioned below the pivoting axis a light-tight covered chute having U-shaped feed hopper, and which leads to the automatic developing arrangement. Into the feed hopper, which is located directly adjacent the X-ray exposure installation, there may be dropped the exposed film sheets coming from the X-ray exposure installation. Due to gravity they then fall into the chute which is located at the lowest point of the feed hopper, and glide along the slide towards the automatic developing arrangement. This construction renders superfluous the need for particular arrangements for receipt of the film sheets from the various inclined and vertical positions of X-ray of the exposure installation.

The extent of friction of the film sheets within the chute is significantly reduced when, in an advantageous embodiment of the invention, there are introduced nozzles supplied with pressurized air in the walls of the chute and the feed hopper. In this manner, the film sheets may glide above the floor of the chute, generally floating on an air cushion, towards the developing automatic arrangement.

BRIEF DESCRIPTION OF THE DRAWINGS

Further details of the invention may now be ascertained in connection with two illustrative exemplary embodiments, taken in conjunction with the accompanying drawings; in which.

DETAILED DESCRIPTION

Figure 1:
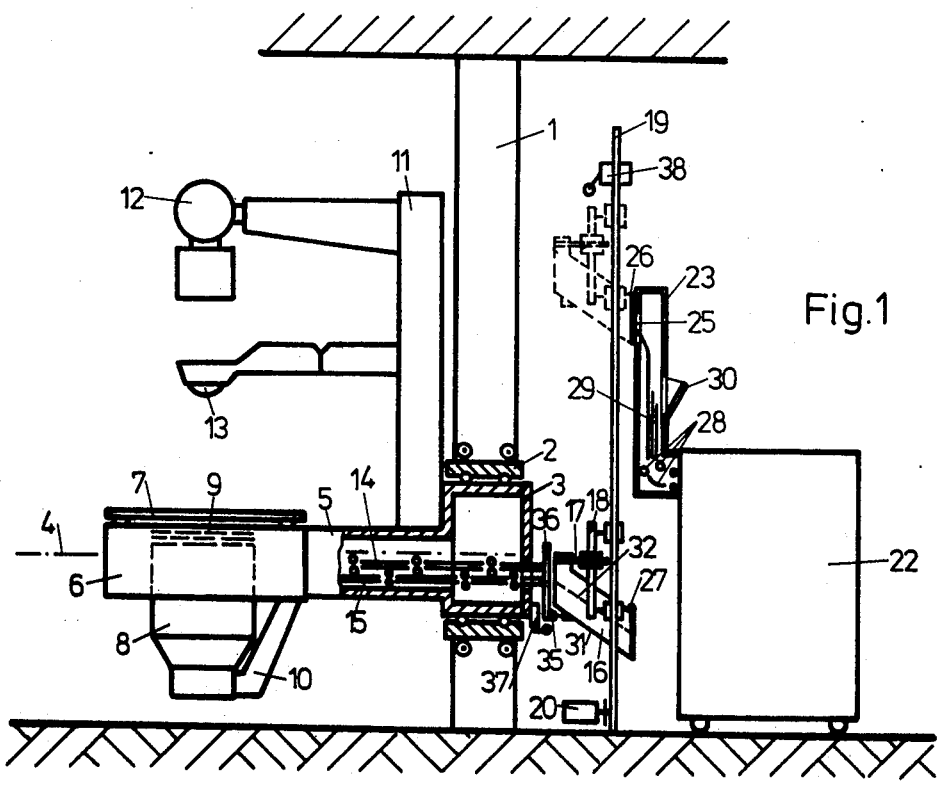
FIG. 1 illustrates the side view of an inventive operative location in which exposed film sheets are conveyed through a tubularly-shaped pivoting axis of an X-ray examining apparatus through into a tiltable and vertically adjustable intermediate magazine in an automatic developing arrangement.

From FIG. 1 there may be ascertained a collar 2 which is vertically adjustable along a separating wall 1, and in which a bearing ring 3 is supported so as to be rotatable about a horizontal pivoting axis 4. Onto the bearing ring there is fastened a carrier 5 for an X-ray exposure installation 6. The X-ray exposure installation has a longitudinally and transversely displaceable patients' support bed or pallet 7 supported thereon. Within the X-ray exposure installation there is also located a picture-intensifying video installation 8, an arrangement 9 for direct X-ray exposures, as well as an arrangement 10 for photographing of the image-intensifying output fluorescent screen, a so-called indirect film exposure system. On the carrier 5 there is also mounted an X-ray tube stand 11 for an X-ray tube 12, and a compression tube or hood 13 which is slidable along the stand. Interiorly of the support there are located conveying runs 14, 15 for the exposed film sheets of the respective direct and the indirect exposure systems. At the terminating point of these conveying runs, at the side of the bearing ring 3 which is remote from the X-ray exposure installation, there is located a stopping location for an intermediate magazine 16. The intermediate magazine suspended from a carriage 18 so as to be rotatable about a horizontal support axis 17, and with the carriage 18 being movable in a vertical direction along a frame 19. The support axis 17 is located above the center of gravity of the intemediate magazine 16. Onto the frame 19 there is fastened a motor 20 having a cable winch 21 (FIG. 2), by means of which the carriage 18 together with the intermediate magazine may be vertically displaced. On the side of the intermediate magazine facing away from the X-ray examining apparatus, there is located an automatic developing arrangement 22, which includes a collecting magazine 23 positioned immediately ahead thereof.

Figure 2:
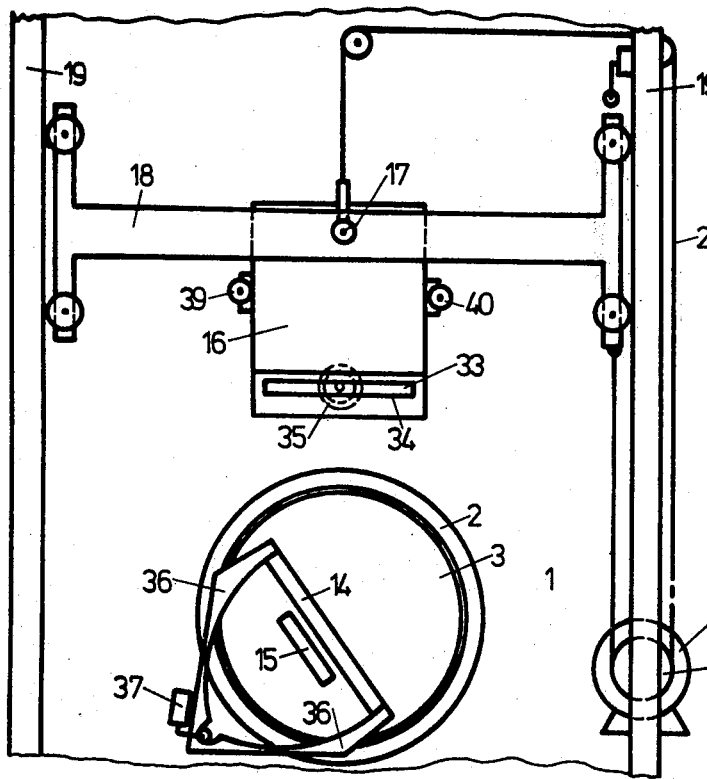
FIG. 2 is an enlarged detail of the intermediate magazine of FIG. 1 and its guidance as viewed from the automatic developing arrangement.

FIG. 2 illustrates the support of the intermediate magazine 16 as viewed from the automatic developing arrangement 22. The intermediate magazine is suspended on carriage 18 so as to be pivotable about horizontal support axis 17. The carriage 18 is supported to be movable along the frame 19 in a vertical direction, and is adjusted in elevation by means of motor 20 through the intermediary of the cable 24 of the cable winch 21. This auxiliary magazine is so movable from a lower loading position, in which it is connected to the conveying runs 14, 15 (FIG. 1) of the X-ray examining apparatus, into an unloading position as shown in chain-dotted lines in FIG. 1, as to be positioned in front of an infeed aperture 25 in the collecting magazine 23 of the automatic developing arrangement 22. The infeed aperture of the collecting magazine may be light-tight closed by means of a slide 26 which may be slid upwardly through a contact stop 27 upon attachment of the intermediate magazine. Interiorly of the collecting magazine 23 there is located a film sheet withdrawal arrangement 28, which is only schematically shown indicated for purposes of clarity, and which is driven by the automatic developing arrangement 22, by means of which the stored film sheets 29 are withdrawn in conformance with the operating speed of the automatic developing arrangement and transferred into the automatic developing arrangement. In addition thereto, the collecting magazine is provided with a closeable feed hopper 30 for the separate insertion of otherwise exposed film sheets.

The intermediate magazine 16, whose support surfaces 31, 32 for the film sheets of, respectively, the direct and indirect systems are in the unloading position at the collecting magazine 23 inclined approximately 45° with respect to the horizontal, is provided on the side at which it is connected to the conveying runs and on the side at which it is connected to the collecting magazine, respectively provided with an infeed and withdrawal slot 34, which is closeable in a light-tight manner by means of a slide 33 (only one illustrated). On the side facing towards the conveying runs, the auxiliary magazine is provided with a roll forming a guide element 35 which, upon approach of the intermediate magazine to the conveying runs 14, 15, engages in a guide bracket 36 which is rigidly mounted on the conveying runs, and which pivots the intermediate magazine 16 into the respective inclined position of the conveying runs. To the guide bracket 36 and at the upper end of the frame 19 there is respectively mounted an end position switch 37, 38 which places the cable winch 21 of the motor 20 in an at-rest position in the unloading and, respectively, unloading positions of the film carriage. On both sides of the intermediate magazine there are mounted magnetic brakes 39, 40 which rigidly couple the intermediate magazine 16 in the loading position to the guide bracket 36.

The exposed film sheets of the direct and indirect systems, which are not described in closer detail are conveyed immediately after exposure along the conveying runs 14, 15, which are provided with the rollers, through the carrier 5 of the X-ray exposure installation 6 and through the bearing ring 3 into the intermediate magazine 16 which is introduced through the guide bracket of the conveying runs. In this intermediate magazine the exposed film sheets are then at first stored. After the completion of an exposure series, for example, upon change of patients, the intermediate magazine 16 is moved by motor 20 into the more elevated discharge position at the collecting magazine 23. Thereby the intermediate magazine, which is suspended above its center of gravity on the support axis 17, rotates into a position in which the support surfaces 31, 32 for the film sheets are inclined by about 45° with respect to the horizontal. The film outlet slot 34 of the intermediate magazine, which is closed in a light-tight manner by a closure 33, upon reaching the unloading position is pressed up through contact against a stop (not shown). Concurrently, the closure 26 of the collecting magazine 23 is opened through the contact 27 at the intermediate magazine 16 upon coming into the unloading position. The motor 20 for the cable winch 21 is then stopped by the end-position switch 38 which is provided for the unloading position of the intermediate magazine 16. In the unloading position the film sheets located in the intermediate magazine, due to the inclination of the support surfaces 31, 32 for the film sheets, may slide into the collecting magazine 23. From this collecting magazine 23 the film sheets 29 are then conveyed by means of the sheet film withdrawal arrangement 28 of the collecting magazine in conformance with the developing speed of the automatic developing arrangement 22 into the automatic developing arrangement. After the emptying of the intermediate magazine 16, the motor 20 is switched by a timer switch (not shown) into a reversely rotating direction and again lowers the intermediate magazine 16 again into it loading position in front of the conveying runs 14, 15 of the X-ray examining apparatus. Prior to reaching the loading position, the guide element 35 which is located at the lower end of the intermediate magazine 16 is engaged by the funnel-shaped guide bracket 36, which is fastened to the conveying runs 14, 15 and conducted into a locked position, wherein the intemediate magazine is pivoted in the same inclined position in which the conveying runs and the X-ray exposure installation 6 are presently located. In this position, the end-position switch 37 is fastened to the guide bracket switches off the motor 20, and switches in the magnetic couplings 39, 40 located on both sides of the intermediate magazine. The intermediate magazine is now rigidly coupled to the guide bracket 36, and upon displacement of the exposure installation 6, is taken along with the guide bracket 36.

Figure 3:
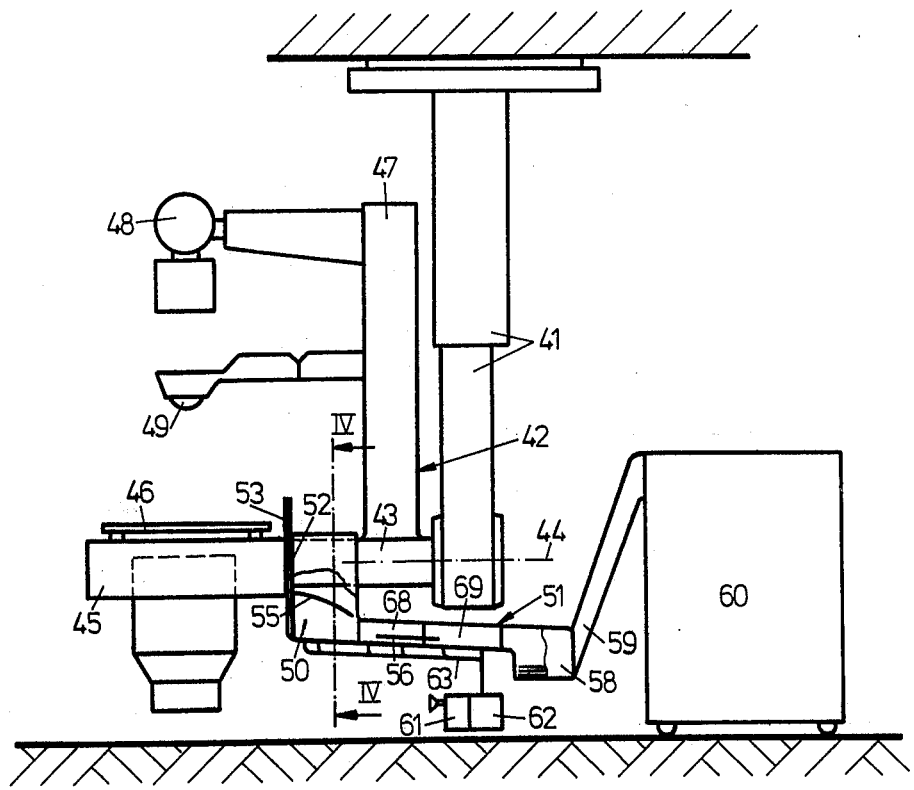
FIG. 3 is a side view of a second embodiment of an inventive operative location in which the exposed film sheets are conveyed from an exposure installation through a slide into an automatic developing arrangement having a preceding collecting magazine attached thereto.

In FIG. 3 there is illustrated an operative location or station with a telescopic-like ceiling support 41 having an X-ray examining apparatus 42 fastened thereto. On the ceiling support 41 there is supported a horizontal carrier 43 for rotation about a horizontal pivoting axis 44, to which there is fastened an X-ray exposure installation 45. Mounted on the X-ray exposure installation is a longitudinally and transversely displaceable patients' support bed or pallet 46. Additionally mounted on the carrier 43 is an X-ray stand 47 including an X-ray tube 48 and a compression tube or hood 49 which is longitudinally displaceable on the X-ray stand. On the side of the X-ray exposure installation 45 facing towards the ceiling support, the carrier 43 of the X-ray exposure installation is in a light-tight manner encompassed by a U-shaped feed hopper 50 which terminates in a chute 51 having inclined or sloped portions.

Figure 4:
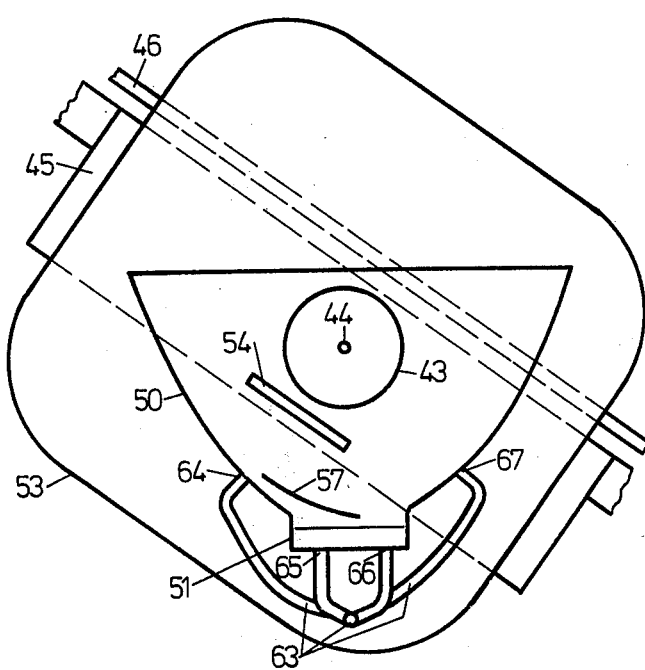
FIG. 4 is a section taken along Line IV—IV in FIG. 3.

The feed hopper 50, which is shown in section in FIG. 4, is open on the side facing towards the X-ray exposure installation 45, and closely adheres in a light-tight manner through a rubber seal 52 to an opaque cover plate 53 which is fastened to the exposure installation on this side of the exposure installation. Within this cover plate there is provided a cutout 54 for the through-passage of the film sheets 56, 55, 57. The chute 51 terminates in a collecting magazine 58 (FIG. 3) which is connected, through the intermediary of a conveying arrangement 59 for the film sheets, with an automatic developing arrangement 60. Below the chute 51 there is provided a pressurized air collector 61 having an electrical discharge line 62 connected thereto. From the discharge line a hose system 63 conducts ionized pressurized air into various nozzles 64, 65, 66, 67 located in the walls of the feed hopper and the chute.

The film sheets 55, 56, 57 which are exposed in the X-ray exposure or filming installation 45 of the X-ray examining apparatus 42, are ejected through the cutout 54 in the cover plate 53 into the feed hopper 50 which is connected to the X-ray exposure installation in a light-tight manner and glide, independently of the particular inclined position of the X-ray exposure installation 45 with respect to the pivoting axis 44, along the wall of the feed hopper 50 into the chute 51 inserted in the lowest point of the feed hopper. Through this chute they then come into the collecting magazine 58 which is fixedly positioned at the end of the chute. In order to reduce the degree of friction along the walls of the chute 51 and the feed hopper 50, nozzles 64, 65, 66 and 67 are located in these walls, by means of which pressurized air generated in the pressurized air collector 61 and ionized in the electrical discharge line 62 is blown interiorly of the chute 51 and the feed hopper 50. Due to the pressurized air, the film sheets which glide along the walls are maintained in a floating position. The friction is thereby reduced to such an extent that the chute 51 with only small inclination is adequate. In the discharge line 62 which is connected to the pressurized air collector 61 the pressurized air is ionized before it is transmitted to the nozzles. Eventual potential differentials present on the film surfaces are rapidly balanced by means of the ionized air. In this embodiment of the X-ray examining apparatus, the feed hopper 50 is no longer pivoted together with the X-ray examining installation 45 about the pivoting axis 44, but is vertically adjusted in conjunction with the pivoting axis. In order to compensate for this lifting movement of the feed hopper, the chute 51 consists of two overlapping roof tile-like sections 68, 69 which are telescopingly slidable into each other and the chute is linkably fastened to the feed hopper, as well as to the collecting magazine 58.

While there has been shown what is considered to be the preferred embodiment of the invention, it will be obvious that modifications may be made which come within the scope of the disclosure of the specification.

What is claimed is:

1. In an operative location for the examination of patients by X-rays, including a patient's support bed tiltable about a horizontal, vertically adjustable pivoting axis; an X-ray exposure installation having a picture plane extending in parallel with said patients' support bed; an overhead X-ray tube oriented towards said picture plane; and an automatic developing arrangement for X-ray film sheets, the improvement comprising: conveying means for the exposed X-ray film sheets compensating for the elevational adjustability and inclinability of said X-ray exposure installation being disposed intermediate said picture plane and said automatic developing arrangement, said developing arrangement being immovably positioned on the floor of said location, said conveying means including a conveying run for said exposed film sheets connected to said X-ray exposure installation and being jointly tiltable therewith about said pivoting axis; and at least one intermediate film sheet storage magazine adapted to be selectively aligned with said conveying run and said developing arrangement, said intermediate magazine being vertically adjustable and rotatable about a support axis extending in parallel with said pivoting axis.

2. An operative location as claimed in claim 1, comprising a guide bracket being mounted on said conveying run; and a guide element being fastened to said intermediate magazine adapted for operative engagement with said guide bracket whereby said intermediate magazine is rotated and centered into the respective inclined position of said conveying run upon approaching the latter.

3. An operative location as claimed in claim 2, comprising coupling means for effecting movement of said intermediate magazine during changes in position of said X-ray exposure installation, said coupling means interconnecting said conveying run and said intermediate magazine.

4. An operative location as claimed in claim 1, comprising a collecting magazine being located directly preceding said automatic developing arrangement for receiving said exposed film sheets.

5. An operative location as claimed in claim 1, said conveying run including a first conveying run for exposed film sheets being directly exposed to the X-rays, and a separate second conveying run extending in parallel to said first conveying run for conveying small-sized film sheets being disposed to an image-intensifying output fluorescent screen, said intermediate magazine having support surfaces coordinated with the varying film sizes, said support surfaces being adapted to be coupled in synchronism with their respective associated conveying runs.

6. An operative location as claimed in claim 1, comprising pressure roll means for retaining said film sheets in said intermediate magazine independently of the positioning thereof.

7. An operative location as claimed in claim 4, said collecting magazine including a film sheet withdrawal arrangement.

8. An operative location as claimed in claim 7, said film sheets being withdrawn from said collecting magazine in an exposure series sequence.

9. In an operative location for the examination of patients by X-rays, including a patients' support bed tiltable about a horizontal, vertically adjustable pivoting axis; an X-ray exposure installation having a picture plane extending in parallel with said patients' support bed; an overhead X-ray tube oriented towards said picture plane, and an automatic developing arrangement for X-ray film sheets, the improvement comprising: conveying means for the exposed X-ray film sheets compensating for the elevational adjustability and inclinability of said X-ray exposure installation being disposed intermediate said picture plane and said automatic developing arrangement, said developing arrangement being immovably positioned on the floor of said location; a light-tight covered chute having a U-shaped feed hopper being located below said pivoting axis and leading towards said automatic developing arrangement; a plurality of nozzles being locaated in the walls of said chute and of said feed hopper; and means for supplying pressurized air to said nozzles.

10. An operative location as claimed in claim 9, comprising an electrical discharge line for ionizing said pressurized air prior to conveyance thereof to said nozzles.

* * * * *